(12) United States Patent
Kambayashi et al.

(10) Patent No.: US 7,928,090 B2
(45) Date of Patent: Apr. 19, 2011

(54) EXTERNAL PREPARATION COMPOSITION

(75) Inventors: Hiroaki Kambayashi, Hiratsuka (JP); Hiroshi Konta, Ichikawa (JP)

(73) Assignee: Lion Corporation, Tokyo (JP)

( * ) Notice: Subject to any disclaimer, the term of this patent is extended or adjusted under 35 U.S.C. 154(b) by 0 days.

(21) Appl. No.: 12/605,294

(22) Filed: Oct. 23, 2009

(65) Prior Publication Data

US 2010/0074856 A1   Mar. 25, 2010

Related U.S. Application Data

(62) Division of application No. 12/257,853, filed on Oct. 24, 2008, now Pat. No. 7,763,595, which is a division of application No. 10/522,032, filed as application No. PCT/JP2002/007549 on Jul. 25, 2002, now abandoned.

(51) Int. Cl.
*A61K 31/70* (2006.01)
*A61K 31/7008* (2006.01)
(52) U.S. Cl. ............. 514/62; 514/25; 536/55.2; 536/4.1
(58) Field of Classification Search .................... 514/62, 514/25; 536/55.2, 4.1
See application file for complete search history.

(56) References Cited

U.S. PATENT DOCUMENTS

| 4,323,561 A | 4/1982 | Nowotny |
| 4,717,720 A | 1/1988 | Shroot et al. |
| 5,075,340 A | 12/1991 | Barua et al. |
| 5,091,522 A | 2/1992 | Philippe et al. |
| 5,096,713 A | 3/1992 | Philippe et al. |
| 5,808,111 A | 9/1998 | Curley et al. |
| 6,221,371 B1 | 4/2001 | Baik et al. |

FOREIGN PATENT DOCUMENTS

| DE | 27 08 667 A1 | 8/1978 |
| JP | 49-20762 B | 5/1974 |
| JP | 62-36306 A | 1/1987 |
| JP | 11-501940 A | 2/1992 |
| JP | 5-139949 A | 6/1993 |
| JP | 2001-39997 A | 2/2001 |
| JP | 2001 039997 A  * | 2/2001 |
| JP | 2001-039997 A | 2/2001 |
| JP | 2001-170028 A | 6/2001 |
| WO | 96/18600 A1 | 6/1996 |
| WO | 99/13859 A1 | 3/1999 |
| WO | 99/50240 A1 | 10/1999 |

OTHER PUBLICATIONS

Matsuda et al. (JP 2001 039997 A, Feb. 13, 2001, Machine English Translation).*
Hayashi et al., "Changes of facial wrinkles by aging, sunlight exposure and application of cosmetics," *J. Soc. Cosmet. Chem. Japan*, 1993, vol. 27, No. 3, pp. 355-373 (partial translation).
*The Nishinihon J. of Derm.* 2001, vol. 63, No. 2, pp. 103-111.
Sakazaki et al., "Optical Investigation of Aging Skin and the Development of Makeup that Restores a Youthful Look," 21st, IFSCC Seminar Lecture Abstract, 2001, pp. 124-128.
English translation of the International Preliminary Examination Report, mailed Jan. 27, 2005 from the International Bureau of WIPO.
Fieser et al., "Synthetic Emulsifying Agents", *Journal of American Chemical Society*, 1956, vol. 78, pp. 2825-2832.
Extended European Search Report dated Dec. 2, 2008 issued in corresponding European Application No. 08002241.1-2108/1917956.
Extended European Search Report dated Dec. 2, 2008 issued in corresponding European Application No. 08002242.9-2108/1941863.
Matsuda et al., (JP 2001-039997 A, Feb. 13, 2001, Machine English Translation).

* cited by examiner

*Primary Examiner* — Shaojia Anna Jiang
*Assistant Examiner* — Michael C Henry
(74) *Attorney, Agent, or Firm* — Buchanan Ingersoll & Rooney PC

(57) ABSTRACT

An external preparation composition used for preventing or treating symptoms or diseases related to dermatopathy caused by dryness, UV rays and aging such as wrinkles and sags of the skin, pigmentation of the skin, skin roughness and coarse texture and skin diseases such as psoriasis, lichen, ichthyosis, keratosis, Darier's disease, pustulosis, acne, eczema and atopic dermatitis. The external preparation composition comprises at least one of acyl glucosamine derivatives represented by the following Formula (I):

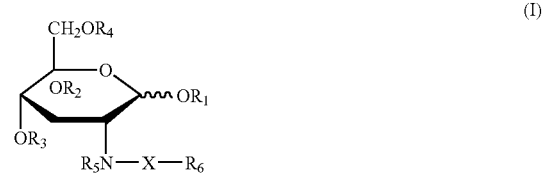

(I)

wherein $R_1, R_2, R_3, R_4$ and $R_5$ are defined; and X is any one of groups represented by the following Formulas (A) to (C):

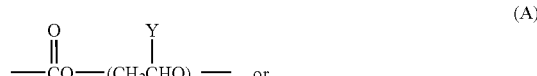

(A)

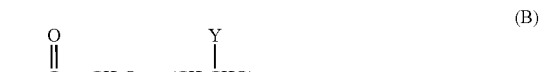

(B)

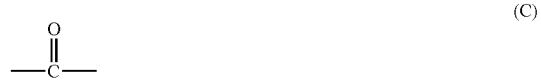

(C)

wherein Y, n and $R_6$ are also defined.

6 Claims, No Drawings

EXTERNAL PREPARATION COMPOSITION

CROSS-REFERENCE TO PRIORITY APPLICATION

This application is a divisional of U.S. application Ser. No. 12/257,853, filed on Oct. 24, 2008, which is a divisional of U.S. application Ser. No. 10/522,032 filed on Jan. 21, 2005, which is a national stage application, filed under 35 U.S.C. §371, of PCT/JP2002/007549, filed on Jul. 25, 2002, all of which are hereby expressly incorporated by reference and assigned to the assignee hereof.

TECHNICAL FIELD

The present invention relates to an external preparation composition for preventing or treating symptoms or diseases related to dermatopathy caused by dryness, UV rays and aging such as wrinkles and sags of the skin, pigmentation of the skin, skin roughness and coarse texture and skin diseases such as psoriasis, lichen, ichthyosis, keratosis, Darier's disease, pustulosis, acne, eczema and atopic dermatitis.

BACKGROUND ART

In general, phenomena such as wrinkles, sags, spots and skin roughness which are caused by aging, UV rays and dryness are well known as factors for damaging the beauty of the skin.

A normal skin looks flat at a glance, but a skin surface has a pattern constituted of fine grooves (sulci cutis) and parts (cristae cutis) surrounded by them, that is, a "texture". The texture is also given as an important factor taking part in the beauty of the skin, and disturbance and a coarseness change in the texture are a large factor for damaging the beauty of the skin.

To observe the role of the texture from a dermatological point of view, sulci cutis provide a corneum having low flexibility with capability to meet dynamic deformation, and they are a passage for sebum and sweat. Accordingly, the skin can maintain smoothness, gloss and flexibility by spreading a lot of the sulci cutis [J. Soc. Cosmet. Chem. Japan, 27 (3), 1993 and The Nishinihon J. of Derm. 63 (2), 103, 2001].

Further, it is known that observing from an optical point of view, conditioned fine texture raises a reflectance on a skin surface and allows the skin to look white (21st, IFSCC Seminar Lecture Abstract, 124, 2001). Not only the texture is coarsened by dryness, but also the beauty of the skin, that is, the smoothness, the gloss, the flexibility and the whiteness of the skin are lost as the age passes, and the skin is notably coarsened and chapped. Further, a relation between the young and beautiful skin and the well-conditioned texture is often pointed out (for example, Japanese Patent Application Laid-Open No. 170028/2001).

Further, skin diseases such as pustulosis, acne, eczema, psoriasis, lichen, ichthyosis, keratosis and atopic dermatitis bring about a serious change in the appearance and the function of the skin.

A lot of medicines and cosmetics which improve the above matters have so far been known. Vitamins A, C, D and derivatives thereof and urea are widely known as the above medicines. Also, used are substances having an epithelium-abrasive action such as α-hydroxy acids including lactic acid and glycolic acid and β-hydroxy acids represented by salicylic acid. Further, carbohydrate derivatives shown in, for example, Japanese translation of PCT international publication for patent application No. 501940/1999) are known as a medicine provided with an epithelium-abrasive action by inhibiting a corneum binding action. On the other hand, amino acids, polyhydric alcohols, polysaccharides, lipids such as ceramides and various ingredients extracted from natural products are blended with skin external preparations as a conventional skin roughness-improving agent for the purpose of providing a moisture holding effect. Further, ellagic acid, kojic acid, arbutin, hydroquinone and various ingredients extracted from natural products have been compounded with conventional whitening agents.

However, medicines and cosmetic compositions blended with the conventional drug efficacy components described above do not still have satisfactory effects on a change in the skin, and the existing situation is that medicines having excellent effects are desired to be developed.

On the other hand, it is known that retinoids including retinoic acid have various and strong physiologic action such as controlling of proliferation and differentiation of cells and controlling of gene expression. It is reported by researches which have so far been made that retinoids have excellent effects for preventing or treating symptoms or diseases related to dermatopathy caused by dryness, UV rays and aging such as wrinkles, sags and pigmentation of the skin and skin diseases such as psoriasis, lichen, ichthyosis, keratosis, Darier's disease, pustulosis, acne, eczema and atopic dermatitis.

However, because of side effects such as strong irritation and teratogenicity and inferior solubility in water, retinoids have so far been extremely limited in application to cosmetics and medicines.

In light of the conventional problems and existing situation described above, the present invention intends to solve them, and an object thereof is to provide an external preparation composition for preventing or treating symptoms or diseases related to dermatopathy caused by dryness, UV rays, active oxygen and aging such as wrinkles and sags of the skin, pigmentation of the skin, skin roughness and coarse texture, dyskeratosis such as psoriasis, lichen, ichthyosis and Darier's disease and skin diseases such as pustulosis, acne, eczema and atopic dermatitis.

Another object of the present invention is to provide an external preparation composition which is useful as at least one of a wrinkle-improving agent, a coarse texture-improving agent, a skin roughness-improving agent, a whitening agent and a acne-improving agent.

DISCLOSURE OF THE INVENTION

Intensive researches repeated by the present inventors have resulted in finding that a specific acyl glucosamine derivative does not have side effects such as irritation and teratogenesis and that it has an excellent effect for dermatopathy and diseases such as wrinkles and sags of the skin, pigmentation of the skin, skin roughness and coarse texture, baldness, psoriasis, lichen, ichthyosis, keratosis, pustulosis, acne, eczema and atopic dermatitis. In particular, intensive researches repeated by the present inventors on action to the skin have resulted in finding a wrinkle-improving effect on the skin in a mouse irradiated with UV rays, a acne-treating effect on acne patients, a coarse texture-improving effect on the skin in a mouse irradiated with UV rays, an improving effect on skin roughness caused by sodium dodecylsulfate (SDS) and a pigmentation-improving effect in a guinea pig irradiated with UV rays, and thus the present invention has come to be completed.

That is, the present invention comprises the following items (1) to (5).

(1) An external preparation composition comprising at least one of acyl glucosamine derivatives represented by the following Formula (I):

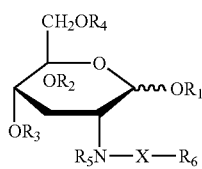
(I)

wherein $R_1$, $R_2$, $R_3$ and $R_4$ represent a hydrogen atom, a saturated or unsaturated, linear or branched fatty acid residue having 2 to 36 carbon atoms or a linear or branched alkyl group having 1 to 4 carbon atoms which may have a hydroxyl group, and they may be the same or different each other; $R_5$ represents a hydrogen atom or a linear or branched alkyl group having 1 to 4 carbon atoms which may have a hydroxyl group; X is any one of groups represented by the following Formulas (A) to (C):

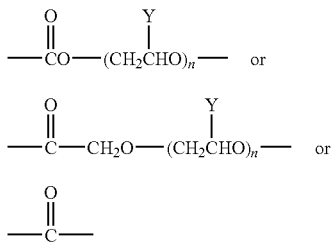

wherein Y in the formulas (A) and (B) described above represents a hydrogen atom or an alkyl group having 1 to 5 carbon atoms in which an ether group may be interposed between a bond; and n represents an integer of 0 to 10; and $R_6$ represents a linear or branched alkyl group or alkenyl group having 11 to 36 carbon atoms which may have a substituent.

(2) The external preparation composition as described in the above item (1), wherein it is used as at least one of a wrinkle-improving agent, a coarse texture-improving agent, a skin roughness-improving agent, a whitening agent and a acne-improving agent.

(3) The external preparation composition as described in the above item (1) or (2), comprising a percutaneous absorption accelerator and/or a chemically active substance having a skin care effect.

(4) The external preparation composition as described in any of the above items (1) to (3), further comprising a silicone oil and a silicone derivative.

BEST MODE FOR CARRYING OUT THE INVENTION

The contents of the present invention shall be explained below in more details.

The external preparation composition of the present invention is characterized by comprising at least one of acyl glucosamine derivatives represented by the following Formula (I):

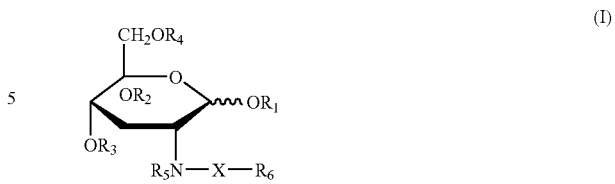
(I)

wherein $R_1$, $R_2$, $R_3$ and $R_4$ represent a hydrogen atom, a saturated or unsaturated, linear or branched fatty acid residue having 2 to 36 carbon atoms or a linear or branched alkyl group having 1 to 4 carbon atoms which may have a hydroxyl group, and they may be the same or different each other; $R_5$ represents a hydrogen atom or a linear or branched alkyl group having 1 to 4 carbon atoms which may have a hydroxyl group; X is any one of groups represented by the following Formulas (A) to (C):

(A)

(B)

(C)

wherein Y in the formulas (A) and (B) described above represents a hydrogen atom or an alkyl group having 1 to 5 carbon atoms in which an ether group may be interposed between a bond; and n represents an integer of 0 to 10; and $R_6$ represents a linear or branched alkyl group or alkenyl group having 11 to 36 carbon atoms which may have a substituent.

In the present invention, the acyl glucosamine derivatives represented by Formula (I) include, for example, N-retinoyl-D-glucosamine, 1,3,4,6-tetra-O-acetyl-N-retinoyl-D-glucosamine, N-retinoyl-6-O-retinoyl-D-glucosamine, N-lauroyl-D-glucosamine, N-myristoyl-D-glucosamine, N-tetradecenoyl-D-glucosamine, N-palmitoyl-D-glucosamine, N-hexadecenoyl-D-glucosamine, N-stearoyl-D-glucosamine, N-isostearoyl-D-glucosamine, N-oleoyl-D-glucosamine, N-linoleoyl-D-glucosamine, N-linolenoyl-D-glucosamine, N-eicosenoyl-D-glucosamine, N-eicosadienoyl-D-glucosamine, N-eicosatrienoyl-D-glucosamine, N-eicosapentaenoyl-D-glucosamine, N-arachidonoyl-D-glucosamine, N-docosanoyl-D-glucosamine, N-docosenoyl-D-glucosamine, N-docosadienoyl-D-glucosamine, N-docosatrienoyl-D-glucosamine, N-docosatetraenoyl-D-glucosamine, N-docosahexaenoyl-D-glucosamine, N-tetracosenoyl-D-glucosamine, N-tetracosadienoyl-D-glucosamine, N-tetracosatrienoyl-D-glucosamine, N-hexacosenoyl-D-glucosamine, N-hexacosadienoyl-D-glucosamine, N-hexacosatrienoyl-D-glucosamine, N-octacosenoyl-D-glucosamine, N-dotriacontenoyl-D-glucosamine, N-hexatriacontenoyl-D-glucosamine, 1,3,4,6-tetra-O-acetyl-N-lauroyl-D-glucosamine, N-lauroyl-6-O-lauroyl-D-glucosamine, N-lauroyl-N-methyl-D-glucosamine, 1,3,4,6-tetra-O-methyl-N-methyl-N-lauroyl-D-glucosamine, N-(2-hydroxyethyl)-N-linolenoyl-D-glucosamine, 1,3,4,6-tetra-O-(2-hydroxyethyl)-N-(2-hydroxyethyl)-N-oleoyl-D-glucosamine, N-palmitoyl-N-(2-hydroxyethyl)-3,4,5-O-(2- hydroxyethyl)-D-glucosamine, N-dodecyloxycarbonyl-D-glucosamine, N-tetradecyloxycarbonyl-D-glucosamine, N-hexadecyloxycarbonyl-D-glucosamine, N-octadecyloxycarbonyl-D-glucosamine, N-monooxyethylenedodecyletheroxycarbonyl-D-glucosamine, N-dioxyethylenedodecyletheroxycarbonyl-D-glucosamine, N-trioxyethylenetetradecyletheroxycarbonyl-D-glucosamine, N-tetraoxyethylenehexadecyletheroxycarbonyl-D-glucosamine, N-POE(2)dodecyletheroxycarbonyl-D-glucosamine, N-POE(2)hexadecyletheroxycarbonyl-D-glucosamine, N-POE(5)octadecyletheroxycarbonyl-D-glucosamine, N-POE(10)docosyletheroxycarbonyl-D-glucosamine, N-monooxyethylenedodecyletheroxyacetyl-D-glucosamine, N-trioxyethylenedodecyletheroxyacetyl-D-glucosamine, N-tetraoxyethylenehexadecyletheroxyacetyl-D-glucosamine, N-POE(2)dodecyletheroxyacetyl-D-glucosamine, N-POE(2)hexadecyletheroxyacetyl-D-glucosamine, N-POE(5)octadecyletheroxyacetyl-D-glucosamine and N-POE(10)docosyletheroxyacetyl-D-glucosamine.

Among them, it is preferred in terms of providing further effects that all of $R_1$ to $R_5$ are hydrogen atoms and that $R_6$ may have a substituent and has 11 to 36 carbon atoms, and preferred are, for example, N-retinoyl-D-glucosamine, N-lauroyl-D-glucosamine, N-myristoyl-D-glucosamine, N-tetradecenoyl-D-glucosamine, N-palmitoyl-D-glucosamine, N-hexadecenoyl-D-glucosamine, N-stearoyl-D-glucosamine, N-isostearoyl-D-glucosamine, N-oleoyl-D-glucosamine, N-linoleoyl-D-glucosamine, N-linolenoyl-D-glucosamine, N-eicosenoyl-D-glucosamine, N-eicosadienoyl-D-glucosamine, N-eicosatrienoyl-D-glucosamine, N-eicosapentaenoyl-D-glucosamine, N-arachidonoyl-D-glucosamine, N-docosanoyl-D-glucosamine, N-docosenoyl-D-glucosamine, N-docosadienoyl-D-glucosamine, N-docosatrienoyl-D-glucosamine, N-docosatetraenoyl-D-glucosamine, N-docosahexaenoyl-D-glucosamine, N-tetracosenoyl-D-glucosamine, N-tetracosadienoyl-D-glucosamine, N-tetracosatrienoyl-D-glucosamine, N-hexacosenoyl-D-glucosamine, N-hexacosadienoyl-D-glucosamine, N-hexacosatrienoyl-D-glucosamine, N-octacosenoyl-D-glucosamine, N-dodecyloxycarbonyl-D-glucosamine, N-tetradecyloxycarbonyl-D-glucosamine, N-hexadecyloxycarbonyl-D-glucosamine, N-octadecyloxycarbonyl-D-glucosamine, N-monooxyethylenedodecyletheroxycarbonyl-D-glucosamine, dioxyethylenedodecyletheroxycarbonyl-D-glucosamine, N-trioxyethylenetetradecyletheroxycarbonyl-D-glucosamine, N-tetraoxyethylenehexadecyletheroxycarbonyl-D-glucosamine, N-POE(2)dodecyletheroxycarbonyl-D-glucosamine, N-POE(2)hexadecyletheroxycarbonyl-D-glucosamine, N-POE(5)octadecyletheroxycarbonyl-D-glucosamine, N-POE(10)docosyletheroxycarbonyl-D-glucosamine, N-monooxyethylenedodecyletheroxyacetyl-D-glucosamine, N-trioxyethylenedodecyletheroxyacetyl-D-glucosamine, N-tetraoxyethylenehexadecyletheroxyacetyl-D-glucosamine, N-POE(2)dodecyletheroxyacetyl-D-glucosamine, N-POE(2)hexadecyletheroxyacetyl-D-glucosamine, N-POE(5)octadecyletheroxyacetyl-D-glucosamine and N-POE(10)docosyletheroxyacetyl-D-glucosamine.

Particularly preferred are N-retinoyl-D-glucosamine, N-lauroyl-D-glucosamine, N-myristoyl-D-glucosamine, N-palmitoyl-D-glucosamine, N-stearoyl-D-glucosamine, N-isostearoyl-D-glucosamine, N-tetradecenoyl-D-glucosamine, N-hexadecenoyl-D-glucosamine, N-oleoyl-D-glucosamine, N-linoleoyl-D-glucosamine, N-linolenoyl-D-glucosamine, N-eicosenoyl-D-glucosamine, N-eicosadienoyl-D-glucosamine, N-eicosatrienoyl-D-glucosamine, N-eicosapentaenoyl-D-glucosamine, N-arachidonoyl-D-glucosamine, N-docosanoyl-D-glucosamine, N-docosenoyl-D-glucosamine, N-docosadienoyl-D-glucosamine, N-docosatrienoyl-D-glucosamine, N-docosatetraenoyl-D-glucosamine, N-docosahexaenoyl-D-glucosamine, N-dodecyloxycarbonyl-D-glucosamine, N-tetradecyloxycarbonyl-D-glucosamine, N-hexadecyloxycarbonyl-D-glucosamine, N-octadecyloxycarbonyl-D-glucosamine, N-monooxyethylenedodecyletheroxycarbonyl-D-glucosamine, dioxyethylenedodecyletheroxycarbonyl-D-glucosamine, N-trioxyethylenetetradecyletheroxycarbonyl-D-glucosamine, N-tetraoxyethylenehexadecyletheroxycarbonyl-D-glucosamine, N-POE(2)dodecyletheroxycarbonyl-D-glucosamine, N-POE(2)hexadecyletheroxycarbonyl-D-glucosamine, N-POE(5)octadecyletheroxycarbonyl-D-glucosamine, N-POE(10)docosyletheroxycarbonyl-D-glucosamine, N-monooxyethylenedodecyletheroxyacetyl-D-glucosamine, N-trioxyethylenedodecyletheroxyacetyl-D-glucosamine, N-tetraoxyethylenehexadecyletheroxyacetyl-D-glucosamine, N-POE(2)dodecyletheroxyacetyl-D-glucosamine, N-POE(2)hexadecyletheroxyacetyl-D-glucosamine, N-POE(5)octadecyletheroxyacetyl-D-glucosamine and N-POE(10)docosyletheroxyacetyl-D-glucosamine.

The various acyl glucosamine derivatives described above which are used in the present invention can be obtained by conventional methods, and they can be synthesized on conditions described in, for example, J. Am. Chem. Soc., 78, 2825 (1956).

In the present invention, the various acyl glucosamine derivatives represented by Formula (I) described above can be used in a single kind (each alone) or in suited combination of two or more kinds thereof.

The acyl glucosamine derivatives in the present invention can suitably be used for an external preparation composition. In this case, a content of the whole substances described above is preferably 0.0001 to 10% by mass (hereinafter referred to merely as "%"), particularly preferably 0.001 to 5% based on the total amount of the external preparation composition.

If the above content is less than 0.0001%, the effects of the present invention are less likely to be sufficiently exhibited. On the other hand, if the content exceeds 10%, further improvement in the effects can not be observed.

The effects of the present invention can not be exerted by acyl glucosamine derivatives which are not included in Formula (I) described above.

Further, it has become clear that when $R_6$ in the acyl glucosamine derivative represented by Formula (I) described above is retinoid, a solubility thereof in the preparation is improved if the cis type stereoisomer is contained in a proportion of 0.5% or more based on the trans type. The above cis type stereoisomer includes, for example, at least one of 7-cis, 9-cis, 11-cis, 13-cis, 7,9-di-cis, 9,13-di-cis, 11,13-di-cis and 7,9,13-tri-cis. Accordingly, in the present invention, when $R_6$ in the acyl glucosamine derivative represented by Formula (I) described above is retinoid, at least one of the cis type stereoisomers described above is preferably contained in a proportion of 0.5% or more based on the trans type from the viewpoint of further increase in the solubility.

The external preparation composition of the present invention further comprises a percutaneous absorption accelerator and/or a chemically active substance having a skin care effect, whereby the effects of the present invention can further be improved.

The percutaneous absorption accelerator which can be used in the present invention shall not specifically be restricted as long as it is usually blended with skin external preparations (medicines, quasidrugs and cosmetics).

The percutaneous absorption accelerator which can be used specifically includes, for example, (1) ester oils having high affinity to the skin, for example, isopropyl palmitate, isopropyl myristate, diisopropyl adipate, dioctyl succinate and octyldodecyl lactate, (2) fatty acids or esters thereof having a double bond which positively acts on a structure of intercellular lipid, for example, oleic acid, ethyl oleate, decyl oleate, oleyl oleate, octyldodecyl oleate and propylene glycol oleate, (3) substances having protein denaturation action which acts on keratin protein, for example, urea and derivatives thereof, glycolic acid and salts thereof, lactic acid and salts thereof and salicylic acid, (4) substances which change a distribution ratio of effective ingredients onto the skin, for example, alcohols (ethanol and isopropanol) and polyhydric alcohols (propylene glycol, dipropylene glycol, 1,3-butylene glycol and polyethylene glycol), (5) polymer percutaneous absorption accelerators which raise retentivity of ingredients on the skin, for example, cyclodextrin and polyethylene glycol/polydimethylsiloxane copolymers and creatinine described in Japanese Patent Application Laid-Open No. 114701/2001. The above percutaneous absorption accelerators can be used alone or in a mixture of two or more kinds thereof.

The preferred percutaneous absorption accelerators are isopropyl palmitate, oleic acid and derivatives thereof, urea and derivatives thereof, glycolic acid and derivatives thereof, salicylic acid and derivatives thereof, ethanol, propylene glycol, dipropylene glycol, 1,3-butylene glycol, polyethylene glycol and creatinine.

A content of the above percutaneous absorption accelerators varies depending on the kind of the percutaneous absorption accelerators and the type of the preparation, and it is preferably 0.01 to 15%, more preferably 0.1 to 10% based on the total amount of the external preparation composition.

If a content of the above percutaneous absorption accelerator is less than 0.01%, the effects of the present invention are not exerted further more. On the other hand, if the above accelerator is added in excess of 15%, the effects of the present invention are not so different, and the stability of the skin cosmetic is inhibited in a certain case.

Various causes act multiply on skin troubles, and therefore it is effective as well for improving the skin condition to combine a variety of the components described above. Accordingly, the components described above can freely be combined as well for other purposes than prescribed above, and the chemically active substances described above may be used alone or in combination of two or more kinds thereof.

The chemically active substance having a skin care effect which can be used in the present invention includes various kinds of conventionally known compounds, for example, drug efficacy substances and physiologically active substances.

The above drug efficacy substances and/or physiologically active substances include substances revealing effects such as whitening, improving wrinkles, accelerating blood circulation, controlling sebum, preventing acnes, preventing skin roughness and anti-inflammation.

The whitening substance includes, for example, retinoic acid, ellagic acid, hydroquinone and derivatives thereof, kojic acid, L-ascorbic acid and derivatives thereof, placenta extracts and 4-n-butylresorcinol, and ellagic acid, arbutin, kojic acid and water-soluble placenta extracts are particularly preferred.

The wrinkle-improving substance includes, for example, pantothenic acid, pantothenic acid derivatives and salts thereof, coenzyme A, oxidizing Coenzyme A and salts thereof, retinoic acid, vitamin A, vitamin A derivatives and salts thereof, marine algae extracts excluding brown algae, hyaluronic acid and salts thereof, an NMF component, amino acid and amino acid derivatives and α-hydroxy acid.

The sebum-controlling substance includes, for example, oil-soluble Licorice extracts, Cumaceba extracts, Siam rosewood extracts, Blue mallow extracts, Swertia herb extracts, Maackia amurensis extracts, vitamin A, vitamin A derivatives and retinoic acid.

The anti-inflammatory substance and the skin roughness-preventing substance include, for example, allantoin, glycyrrhetic acid and derivatives thereof, glycyrrhizic acid and derivatives thereof, urea, lysozyme chloride, guaiazulene and γ-oryzanol.

The acne-preventing•improving substance includes, for example, salicylic acid, pyrocton olamin, vitamin A derivatives thereof, retinoic acid, photosensitizers, oil-soluble Licorice extracts, Cumaceba extracts, Siam rosewood extracts and Blue mallow extracts.

A content of the above chemically active substances having a skin care effect varies depending on the components selected, and in the case of the external preparations of emulsified and solubilized systems, it is, as a standard, preferably 0.001 to 20%, more preferably 0.05 to 10% based on the total amount of the external preparation composition.

If a content of the above chemically active substances is less than 0.001%, the skin care effect is insufficiently exerted. On the other hand, if the above substance is added in excess of 20%, the effects thereof are not so different.

Further, in the external preparation composition of the present invention, the following silicone oils and silicone derivatives are efficiently used as a surfactant, a gelatinizing agent and a base agent, whereby the preparation which has less skin irritation and which is expected further effects can be obtained.

The silicone oils which can be used may be any of a linear type and a cyclic type and can be used regardless of a molecular weight. Also, they may be volatile or non-volatile. Further, they may be of a low viscosity or may be a wax, and they shall not specifically be restricted in elasticity and can be used according to the targeted preparation forms.

The silicone derivatives which can be used include a polyoxyalkylene-added type and an organopolysiloxane type. They include, for example, polyoxyalkylene-modified silicone, polyoxyalkylene-modified organopolysiloxane, polyoxyalkylene•alkyl-co-modified organopolysiloxane and elastomer solid organopolysiloxane. The polymer parts may be cross-linked, and they may be any of a wholly cross-linked type and a partially cross-linked type. Further, they may be copolymers such as alkyl methicone copolyols and alkyl dimethicone copolyols.

The above silicone oils and silicone derivatives may be used alone or in combination of a plurality thereof.

The total content of the above silicone oil and silicone derivative varies depending on the kind thereof and the type of the preparation, and it is preferably 3 to 50%, more preferably 5 to 30% based on the total amount of the external preparation composition.

If a content of the above silicone oil and silicone derivative is less than 0.01%, the effects of the present invention are not exerted further more. On the other hand, if the above agent is added in excess of 50%, the effects of the present invention are not so different, and the stability of the skin cosmetic is inhibited in a certain case.

The external preparation composition of the present invention can suitably be used in the fields of cosmetics, medicines and quasidrugs, and in particular, it can suitably be used as at least one of a wrinkle-improving agent, a coarse texture-improving agent, a skin roughness-improving agent, a whitening agent and a acne-improving agent. In this case, the acyl glucosamine derivative described above can further contain in suited amounts other components usually used for external preparations such as cosmetics and quasidrugs, for example, a moisture holding agent, alcohol, a thickener, an antioxidant, a pH-controlling agent, an antiseptic agent, a perfume, a pigment, a whitening agent, a UV absorber, a UV-scattering agent, vitamins and amino acids as well as an oil component, water and a surfactant in addition to the percutaneous absorption accelerator and/or the chemically active substance having a skin care effect, the silicone oil and the silicone derivative which are preferably added, as long as the effects of the present invention are not damaged.

EXAMPLES

Next, the present invention shall be explained below in further details with reference to test examples, examples and comparative examples, but the present invention shall not be restricted to the examples described below. "%" in the following examples and tables is % by mass.

Test Example 1

Continuous Irritative Test of Guinea Pig Skin

Each left and right two spots (4 spots/head) of applying parts having a frame of 2 cm×2 cm were provided on the back of a shaved guinea pig (Hartley series, 7 weeks of age, female, N=10), and each 50 μL of an ethanol/propylene glycol (7:3) solution containing 0.5% of the respective acyl glucosamine derivatives shown in the following Table 1 was applied once a day on the respective frames.

A skin irritative score after application for 3 days straight was evaluated according to the following evaluation criteria (Draize method). The above irritative score was shown by the total points (full marks: 8 points) of erythema and edema.

Solubility of the acyl glucosamine derivatives shown in the following Table 2 in the ethanol/propylene glycol (7:3) solvent was prescribed according to evaluation criteria (Japanese Pharmacopoeia) by a degree at which the above pulverized derivative was dissolved in the solvent at 20° C. within 30 minutes when it was strongly shaken every 5 minutes for 30 seconds.

The results thereof are shown in the following Table 1 and Table 2.

Evaluation Criteria of Skin Irritative Score:
Erythema:
Evaluation Point
0: no erythema
1: very weak erythema
2: clear erythema
3: middle to strong erythema
4: very strong erythema to crust
Edema:
Evaluation Point
0: no edema
1: very slight edema formation
2: slight edema formation
3: middle edema formation
4: strong edema formation Evaluation Criteria of Solubility:

| Evaluation criteria of solubility: | |
| --- | --- |
| Evaluation point: | Amount of the solvent required for dissolving 1 g or 1 ml of the solute |
| ◉: freely soluble | 1 ml or more and less than 10 ml |
| ○: soluble | 10 ml or more and less than 100 ml |
| Δ: slightly soluble | 100 ml or more and less than 1000 ml |
| X: very slightly soluble | 1000 ml or more and less than 10000 ml |

TABLE 1

| Tested substance | Draize score |
| --- | --- |
| Retinoic acid | 8.0 |
| N-retinoyl-D-glucosamine (9-cis isomer/13-cis isomer/trans isomer = 0.25/0.25/99.5) | 0.1 |
| 1,3,4,6-tetra-O-acetyl-N-retinoyl-D-glucosamine | 0.0 |
| N-oleoyl-D-glucosamine | 0.2 |
| N-linoleoyl-D-glucosamine | 0.3 |
| N-lauroyl-D-glucosamine | 0.1 |
| N-isostearoyl-D-glucosamine | 0.1 |
| N-retinoyl-D-glucosamine (9-cis isomer/13-cis isomer/trans isomer = 0.25/0.25/99.5): N-lauroyl-D-glucosamine = 1:3 | 0.5 |
| N-retinoyl-D-glucosamine (9-cis isomer/13-cis isomer/trans isomer = 0.25/0.25/99.5): N-isostearoyl-D-glucosamine = 1:3 | 0.4 |
| N-POE (2) hexadecyletheroxycarbonyl-D-glucosamine | 0.1 |
| N-POE (5) octadecyletheroxycarbonyl-D-glucosamine | 0.2 |
| N-POE (10) docosyletheroxycarbonyl-D-glucosamine | 0.1 |

TABLE 2

| Tested substance | Stereoisomer ratio | Solubility | Draize score |
| --- | --- | --- | --- |
| N-retinoyl-D-glucosamine | 9-cis isomer/13-cis isomer/trans isomer = 0.25/0.25/99.5 | ○ | 0.1 |
| | 9-cis isomer/trans isomer = 0.5/99.5 | ○ | 0.1 |
| | 13-cis isomer/trans isomer = 0.5/99.5 | ○ | 0.0 |
| | cis isomer/trans isomer = 0/100 | Δ | 0.0 |
| 1,3,4,6-tetra-O-acetyl-N-retinoyl-D-glucosamine | 9-cis isomer/13-cis isomer/isomer = 0.25/0.25/99.5 | ○ | 0.0 |
| | 9-cis isomer/trans isomer = 0.5/99.5 | ○ | 0.0 |
| | 13-cis isomer/trans isomer = 0.5/99.5 | ○ | 0.0 |
| | cis isomer/trans isomer = 0/100 | Δ | 0.0 |

As apparent from the results shown in Table 1 described above, it has become clear that the acyl glucosamine derivatives of the present invention have very weak skin irritation as compared with that of retinoic acid.

Further, as apparent from the results shown in Table 2 described above, when the acyl glucosamine derivative is a retinoyl glucosamine derivative, a retinoyl glucosamine derivative in which a cis type stereoisomer accounts for 0.5% has excellent solubility than that of a retinoyl glucosamine derivative in which a trans type stereoisomer accounts for 100%. Further, in respect to the kind of the above cis type stereoisomer, 9-cis isomer/13-cis isomer=1/1 was best in solubility, and therefore the retinoyl glucosamine derivative in which 9-cis isomer/13-cis isomer/trans isomer was 0.25/0.25/99.5 was used in Test Example 2 and the successive test that described later.

Test Example 2

Wrinkle-Improving Test

Four (4) hairless mice per 1 group (hos: HR-1, 10 weeks of age, female) were irradiated on the back skin once a day with UVB at 50 mJ/cm$^2$ five times a week over a period of 10 weeks. After finishing irradiation, each 100 μL of an ethanol/propylene glycol (7:3) solution containing 0.05% of various acyl glucosamine derivatives shown in the following Table 3 was applied on the mouse back in a frequency of once a day and five times a week over 8 weeks.

After finishing application for 8 weeks, the degree of wrinkles was visually evaluated according to the following evaluation criteria and calculation equation. A control group applied with the ethanol/propylene glycol (7:3) solution was evaluated as a control in the same manner.

Evaluation Criteria of the Degree of Wrinkles:

Evaluation point 0: a lot of fine striations is present on the back and the flank; fine striations run in a direction from the head to the tail; and the striations appear or disappear with the motion of the mouse.

Evaluation point 1: all fine striations along the spine are not observed; a few shallow and coarse wrinkles run perpendicularly to the head-to-tail direction; and the striations appear or disappear with the motion of the mouse.

Evaluation point 2: all fine striations are not observed; slightly coarse wrinkles run perpendicularly to the head-to-tail direction; and the striations are fixed and do not depend on the motion of the mouse.

Evaluation point 3: all fine striations are not observed; some deep wrinkles run perpendicularly to the head-to-tail direction; and the striations are fixed and do not depend on the motion of the mouse.

The respective bodies were evaluated by an evaluation point of a 0.5 unit to calculate an average point for the respective groups, and the wrinkle-improving rate was calculated for the respective groups according to the following equation (II). The evaluation results thereof are shown in the following Table 3.

Wrinkle-improving rate (%)=[(average value of the control group−average value of a glucosamine derivative-applied group)/(average value of the control group)]×100       (II)

TABLE 3

| Tested substance | Wrinkle-improving rate |
| --- | --- |
| Control | 0 |
| N-retinoyl-D-glucosamine | 89 |
| N-oleoyl-D-glucosamine | 65 |
| N-linoleoyl-D-glucosamine | 62 |
| N-lauroyl-D-glucosamine | 78 |
| N-isostearoyl-D-glucosamine | 80 |
| N-retinoyl-D-glucosamine:N-lauroyl-D-glucosamine = 1:3 | 93 |
| N-retinoyl-D-glucosamine:N-isostearoyl-D-glucosamine = 1:3 | 92 |
| N-POE (2) hexadecyletheroxycarbonyl-D-glucosamine | 72 |

TABLE 3-continued

| Tested substance | Wrinkle-improving rate |
| --- | --- |
| N-POE (5) octadecyletheroxycarbonyl-D-glucosamine | 73 |
| N-POE (10) docosyletheroxycarbonyl-D-glucosamine | 82 |

As apparent from the results shown in Table 3 described above, it has become clear that the acyl glucosamine derivatives of the present invention have an excellent wrinkle-improving effect.

Side effects such as skin irritation and teratogenicity were not observed at all in all compounds.

Test Example 3

Coarse Texture-Improving Test

Four (4) hairless mice per 1 group (hos: HR-1, 10 weeks of age, female) were irradiated on the back skin once a day with UVB at 40 mJ/cm$^2$ three times a week over a period of 6 weeks. After finishing irradiation, each 100 μL of an ethanol/propylene glycol (7:3) solution containing 0.05% of various acyl glucosamine derivatives shown in the following Table 4 or an ethanol/propylene glycol (7:3) solution as a control was applied on the mouse back in a frequency of once a day and five times a week over 4 weeks.

After finishing application, a replica agent (brand name SILFLO®; manufactured by UK FLEXICO DEVELOPMENTS LTD.) was used to obtain a replica of a mouse back skin. A replica of a UV-non-irradiated group (4 heads) was obtained as a control in the same manner.

The enlarged photographs of the respective replicas were taken through a macro lens (magnification: four times), and the photographs were used to evaluate "coarsening of the texture".

The coarseness of the texture was defined by a "number of texture intersection point", wherein a point in which three or more sulci cutis are joined is counted as one intersection point, and the number of the texture intersection points present in a square of 1 cm×1 cm was counted on the replica photograph.

An average point for the respective groups was calculated, and the texture-improving rate was calculated according to the following equation (III). The evaluation results thereof are shown in the following Table 4.

Texture-improving rate (%)=[(number of texture intersection of applied group)/(number of texture intersection point of non-irradiated group)]×100       (III)

TABLE 4

| Tested substance | Texture-improving rate |
| --- | --- |
| Control | 24 |
| N-retinoyl-D-glucosamine | 75 |
| N-oleoyl-D-glucosamine | 59 |
| N-linoleoyl-D-glucosamine | 58 |
| N-lauroyl-D-glucosamine | 87 |
| N-isostearoyl-D-glucosamine | 72 |
| N-retinoyl-D-glucosamine:N-lauroyl-D-glucosamine = 1:3 | 83 |
| N-retinoyl-D-glucosamine:N-isostearoyl-D-glucosamine = 1:3 | 80 |
| N-POE (2) hexadecyletheroxycarbonyl-D-glucosamine | 89 |

TABLE 4-continued

| Tested substance | Texture-improving rate |
|---|---|
| N-POE (5) octadecyletheroxycarbonyl-D-glucosamine | 92 |
| N-POE (10) docosyletheroxycarbonyl-D-glucosamine | 88 |

As apparent from the results shown in Table 4 described above, it has become clear that the acyl glucosamine derivatives of the present invention have an excellent effect of improving coarseness of the texture. Side effects such as skin irritation and teratogenicity were not observed at all in all compounds.

Test Example 4

Skin Roughness-Improving Test

A 10% SDS solution was used to artificially form a skin roughness in the inside of a forearm of a human being, and a hydrophilic ointment blended with 0.05% of various acyl glucosamine derivatives shown in the following Table 5 was applied thereon twice a day.

The skin roughness-improving degree observed 3 days later after application was evaluated using a change in a stratum corneum water content as an index. The stratum corneum water content is measured in terms of a conductance ($\mu S$). The improving degree was shown by a relative value, wherein the conductance observed when applying the hydrophilic ointment blended with no acyl glucosamine derivative was set at 100, and the skin roughness-improving rate was calculated according to the following equation (IV). The evaluation results thereof are shown in the following Table 5.

Skin roughness-improving rate (%)=[(conductance observed when applying the ointment blended with the tested substance)/(conductance observed when applying the ointment blended with no tested substance)]×100       (IV)

TABLE 5

| Tested substance | Skin roughness-improving rate |
|---|---|
| No addition | 100 |
| N-retinoyl-D-glucosamine | 127 |
| N-oleoyl-D-glucosamine | 114 |
| N-linoleoyl-D-glucosamine | 115 |
| N-lauroyl-D-glucosamine | 114 |
| N-isostearoyl-D-glucosamine | 136 |
| N-retinoyl-D-glucosamine:N-lauroyl-D-glucosamine = 1:3 | 168 |
| N-retinoyl-D-glucosamine:N-isostearoyl-D-glucosamine = 1:3 | 175 |
| N-dodecyloxycarbonyl-D-glucosamine | 183 |
| N-POE (2) hexadecyletheroxycarbonyl-D-glucosamine | 139 |
| N-POE (5) octadecyletheroxycarbonyl-D-glucosamine | 128 |
| N-POE (10) docosyletheroxycarbonyl-D-glucosamine | 138 |

As apparent from the results shown in Table 5 described above, it has become clear that the acyl glucosamine derivatives of the present invention have an excellent skin roughness-improving effect. Side effects such as skin irritation and teratogenicity were not observed at all in all compounds.

Test Example 5

Acne-Improvement Evaluation

Prepared was an essence for acne shown in the following composition example in which 0.05% of various acyl glucosamine derivatives shown in the following Table 6 was blended. An essence which was not blended with an acyl glucosamine derivative was prepared as a control.

| Composition of essence for acne | |
|---|---|
| Acyl glucosamine derivative | 0.05% |
| POE (40)-hardened castor oil | 0.5 |
| Carboxyvinyl polymer (molecular weight: 1,000,000 to 1,500,000) | 0.2 |
| Xanthan gum | 0.2 |
| 1,3-Butylene glycol | 8.0 |
| Ethanol | 10.0 |
| Sodium citrate | 0.3 |
| Methyl paraben | 0.1 |
| Rose water | 0.5 |
| Triisopropanolamine | 0.1 |
| Perfume | trace amount |
| Purified water | balance |
| Total | 100.0 |

Sixty acne patients were picked up as subjects to apply everyday the respective essences on the faces thereof several times a day, and the therapeutic effect against the acnes was visually evaluated a month later according to four degrees of the following evaluation criteria.

Evaluation Criteria:
  ⊚: notably improved
  ○: improved
  Δ: no change
  x: worsened In the four degree evaluation described above, improvement (○) or better effect (⊚) was regarded as "effective for treating acnes", and the subjects showing a treating effect were shown by a numerical value (percentage).

The results thereof are shown in the following Table 6.

TABLE 6

| Tested substance | Evaluation | | | | Acne treating effect |
|---|---|---|---|---|---|
| | ⊚ | ○ | Δ | X | |
| N-retinoyl-D-glucosamine | 4 | 2 | 0 | 0 | 100 |
| N-oleoyl-D-glucosamine | 0 | 3 | 2 | 0 | 60 |
| N-linoleoyl-D-glucosamine | 0 | 1 | 3 | 1 | 20 |
| N-lauroyl-D-glucosamine | 0 | 1 | 1 | 1 | 33 |
| N-isostearoyl-D-glucosamine | 0 | 3 | 2 | 0 | 60 |
| N-retinoyl-D-glucosamine:N-lauroyl-D-glucosamine = 1:3 | 5 | 1 | 0 | 0 | 100 |
| N-retinoyl-D-glucosamine:N-isostearoyl-D-glucosamine = 1:3 | 5 | 0 | 0 | 0 | 100 |
| N-POE (2) hexadecyletheroxycarbonyl-D-glucosamine | 0 | 3 | 2 | 0 | 60 |
| N-POE (5) octadecyletheroxycarbonyl-D-glucosamine | 0 | 2 | 3 | 0 | 40 |
| N-POE (10) docosyletheroxycarbonyl-D-glucosamine | 0 | 2 | 3 | 0 | 40 |

As apparent from the results shown in Table 6 described above, it has become clear that the acyl glucosamine derivatives of the present invention have an excellent acne-improving effect. Side effects such as skin irritation and teratogenicity were not observed at all in all compounds.

Test Example 6

Whitening Evaluation

Back body hair of color guinea pigs were shaved by means of a hair clipper and a shaver, and they were irradiated with UV rays once a day, 4 times a week and 8 times in total, whereby 4 parts of pigmentation having an area of about 2.25 cm$^2$ were formed on the backs of the respective guinea pigs.

Each 30 μL of an ethanol/propylene glycol (7:3) solution containing 0.05% of various acyl glucosamine derivatives shown in the following Table 7 was applied thereon in a frequency of once a day and five times a week over 4 weeks, and a change in the pigmentation was visually evaluated according to four degrees of the following evaluation criteria. The solution containing no acyl glucosamine derivative was used for a comparative example.

Evaluation Criteria of Pigmentation:

+++: notably improved

++: improved

+: a little improved

±: no change

The evaluation results thereof are shown in the following Table 7.

TABLE 7

| Tested substance | Whitening-improving effect |
| --- | --- |
| No addition | ± |
| N-retinoyl-D-glucosamine | +++ |
| N-oleoyl-D-glucosamine | +++ |
| N-linoleoyl-D-glucosamine | ++ |
| N-lauroyl-D-glucosamine | + |
| N-isostearoyl-D-glucosamine | + |
| N-retinoyl-D-glucosamine:N-lauroyl-D-glucosamine = 1:3 | + |
| N-retinoyl-D-glucosamine:N-isostearoyl-D-glucosamine = 1:3 | +++ |
| N-dodecyloxycarbonyl-D-glucosamine | +++ |
| N-POE (2) hexadecyletheroxycarbonyl-D-glucosamine | ++ |
| N-POE (5) octadecyletheroxycarbonyl-D-glucosamine | ++ |
| N-POE (10) docosyletheroxycarbonyl-D-glucosamine | ++ |

As apparent from the results shown in Table 7 described above, it has become clear that the acyl glucosamine derivatives of the present invention have an excellent whitening effect. Side effects such as skin irritation and teratogenicity were not observed at all in all compounds.

As apparent from the results shown in Table 1 to Table 7 described above, it has become clear that the acyl glucosamine derivatives of the present invention have less skin irritation as the external preparation compositions and are excellent in a wrinkle-improving effect, a coarse texture-improving effect, a skin roughness-improving effect, a acne-improving effect and a whitening effect.

Accordingly, the external preparation composition containing at least one of the acyl glucosamine derivatives of the present invention represented by Formula (I) described above is useful as a wrinkle-improving agent, a coarse texture-improving agent, a skin roughness-improving agent, a whitening agent and a acne-improving agent.

Examples 1 to 28

Next, blend compositions are shown in the following Tables 8 to 15 with respect to various uses (lotion, cosmetic gel, cosmetic milky lotion, cosmetic cream, ointment and silicone oil and silicone derivative base-containing cream) and efficacy (wrinkle-improving, coarse texture-improving, skin roughness-improving, whitening and acne-improving) of the external preparation compositions containing the acyl glucosamine derivatives having the respective improving effects described above.

Examples 1 to 5

The respective lotions (for antiwrinkle, texture-improving, skin roughness, acne and whitening) were prepared according to blend compositions shown in the following Table 8.

All lotions were highly effective for preventing or treating the targeted symptoms. Further, they were impregnated into publicly known unwoven fabrics to be used in the form of packs and they were highly effective as well.

TABLE 8

Lotion
(blend unit: % by mass, total amount: 100% by mass)

| | Example | | | | |
| --- | --- | --- | --- | --- | --- |
| | 1 Antiwrinkle | 2 Texture improving | 3 Skin roughness | 4 Acne | 5 Whitening |
| N-retinoyl-D-glucosamine (trans isomer) | 2.00 | 1.00 | 1.00 | 2.00 | 2.00 |
| N-retinoyl-D-glucosamine (9-cis isomer) | 0.001 | 0.005 | 0.001 | | 0.001 |
| N-retinoyl-D-glucosamine (13-cis isomer) | 0.009 | 0.005 | 0.001 | 0.01 | 0.009 |
| N-oleoyl-D-glucosamine | | | 0.50 | | |
| N-linoleoyl-D-glucosamine | | | 0.05 | | 0.05 |
| N-lauroyl-D-glucosamine | 1.00 | 0.50 | | 0.50 | |
| N-isostearoyl-D-glucosamine | 1.00 | 0.50 | | 0.50 | |
| N-POE (2) hexadecyletheroxycarbonyl-D-glucosamine | | 0.10 | 0.05 | | |

TABLE 8-continued

Lotion
(blend unit: % by mass, total amount: 100% by mass)

|  | Example | | | | |
|---|---|---|---|---|---|
|  | 1 Antiwrinkle | 2 Texture improving | 3 Skin roughness | 4 Acne | 5 Whitening |
| N-POE (5) octadecyletheroxy-carbonyl-D-glucosamine | — | — | — | — | 0.05 |
| Decaglyceryl monolaurate | 0.20 | — | — | 0.10 | 0.20 |
| Hexaglyceryl tristearate | — | — | — | 0.10 | — |
| Diglyceryl monoisostearate | 0.1 | — | — | — | 0.10 |
| Polyoxyethylene-hardened castor oil (40E.O.) pyroglutamic acid isostearic acid ester | — | 1.00 | — | — | — |
| Polyoxyethylene sorbitan (20E.O.) monooleate | — | — | 0.50 | — | — |
| Polyoxyethylene oleyl ether (25E.O.) | 0.80 | — | 0.50 | — | 0.80 |
| Polyoxyethylene-hardened castor oil (60E.O.) | — | — | — | 1.00 | — |
| Fermented rice extract | 0.20 | — | — | — | 0.20 |
| Quince seed extract | — | 0.10 | 0.10 | 0.10 | — |
| Peony extract | — | — | 0.10 | 0.10 | — |
| Rose water | 0.10 | — | 0.10 | 0.10 | 0.10 |
| Dipotassium glycyrrhizate | 0.20 | — | — | — | 0.20 |
| Oxidizing Coenzyme A•8 sodium | — | 0.20 | — | — | — |
| Trimethylglycine | — | 1.00 | — | — | — |
| Conc. glycerin | 7.00 | 6.00 | 12.00 | 3.00 | 7.00 |
| 1,3-Butylene glycol | — | 2.00 | 1.00 | 1.00 | — |
| 1,2-Pentanediol | — | — | 0.50 | — | — |
| Carboxyvinyl polymer *1 | — | — | — | — | — |
| Acrylic acid•alkyl methacrylate copolymer *2 | 0.05 | — | — | 0.05 | 0.05 |
| Hydroxyethyl cellulose *3 | — | — | 0.10 | — | — |
| Transparent soluble xanthan gum *4 | — | — | — | 0.05 | — |
| L-arginine | — | — | — | 0.10 | — |
| Methyl paraoxybenzoate | 0.30 | 0.30 | 0.30 | 0.30 | 0.30 |
| Propyl paraoxybenzoate | 0.10 | 0.10 | — | 0.10 | 0.10 |
| Triisopropanolamine | 0.05 | — | — | 0.05 | 0.05 |
| 2-Hydroxy-4-methoxybenzophenone-sulfonic acid trihydrate | 0.10 | — | — | — | 0.10 |
| Ethanol | 12.00 | 8.00 | — | 10.00 | 12.00 |
| Refined water | balance | balance | balance | balance | balance |
| Perfume | trace | trace | trace | trace | trace |

*1: Junron PW111, manufactured by Nippon Junyaku Co., Ltd.
*2: TR-1, manufactured by Goodrich Co., Ltd.
*3: HEC-600, manufactured by Daicel Chemical Industries, Ltd.
*4: Echo Gum, manufactured by Dainippon Pharmaceutical Co., Ltd.

Examples 6 to 10

The respective cosmetic gels (for antiwrinkle, texture-improving, skin roughness, acne and whitening) were prepared according to blend compositions shown in the following Table 9.

All cosmetic gels were highly effective for preventing or treating the targeted symptoms. Further, they were impregnated into publicly known unwoven fabrics to be used in the form of packs and they were highly effective as well.

TABLE 9

Cosmetic gel
(blend unit: % by mass, total amount: 100% by mass)

|  | Example | | | | |
|---|---|---|---|---|---|
|  | 6 Antiwrinkle | 7 Texture improving | 8 Skin roughness | 9 Acne | 10 Whitening |
| N-retinoyl-D-glucosamine (trans isomer) | 2.00 | 1.00 | 1.00 | 2.00 | 2.00 |

TABLE 9-continued

Cosmetic gel
(blend unit: % by mass, total amount: 100% by mass)

|  | Example | | | | |
|---|---|---|---|---|---|
|  | 6 Antiwrinkle | 7 Texture improving | 8 Skin roughness | 9 Acne | 10 Whitening |
| N-retinoyl-D-glucosamine (9-cis isomer) | 0.001 | 0.005 | 0.001 |  | 0.001 |
| N-retinoyl-D-glucosamine (13-cis isomer) | 0.009 | 0.005 | 0.001 | 0.01 | 0.009 |
| N-oleoyl-D-glucosamine |  | 0.05 | 0.05 | 2.00 |  |
| N-linoleoyl-D-glucosamine |  |  |  |  | 0.05 |
| N-lauroyl-D-glucosamine | 1.00 | 0.50 |  | 0.50 |  |
| N-isostearoyl-D-glucosamine |  |  | 1.00 |  |  |
| N-POE (2) hexadecyletheroxy-carbonyl-D-glucosamine |  |  | 0.05 |  |  |
| N-POE (5) octadecyletheroxy-carbonyl-D-glucosamine |  |  |  |  | 0.05 |
| Vegetative squalane | 2.5 | — | — | — | — |
| Polyoxyethylene-hardened castor oil (60E.O.) | — | 0.50 | 0.50 | 0.50 | 0.50 |
| Decaglyceryl monoisolaurate | 2 | — | — | — | — |
| Creatinine | 0.2 | — | — | — | — |
| Marine algae extract powder | 0.2 | — | — | — | — |
| Tocotrienol | 0.1 | — | — | — | — |
| Oil-soluble licorice extract | — | 0.1 | 0.1 | 0.1 | 0.1 |
| Witch hazel extract | 0.1 | — | — | — | — |
| Rose water | 0.1 | — | — | — | — |
| Trimethylglycine | 3 | — | — | — | — |
| Ethanol | — | 7 | 7 | 7 | 7 |
| Conc. glycerin | 1.5 | 1.5 | 1.5 | 1.5 | 1.5 |
| Dipropylene glycol | — | 3 | 3 | 3 | 3 |
| 1,2-Pentanediol | 8 | — | — | — | — |
| Methyl paraoxybenzoate | 0.1 | 0.1 | 0.1 | 0.1 | 0.1 |
| Propyl paraoxybenzoate | 0.1 | 0.1 | 0.1 | 0.1 | 0.1 |
| Transparent soluble xanthan gum *1 | — | 0.1 | 0.1 | 0.1 | 0.1 |
| Acrylic acid•alkyl methacrylate copolymer *2 | 0.2 | 0.3 | 0.3 | 0.3 | 0.3 |
| Triisopropanolamine | 0.15 | 0.18 | 0.18 | 0.18 | 0.18 |
| Citric acid | 0.05 | 0.05 | 0.05 | 0.05 | 0.05 |
| Sodium citrate | 0.05 | 0.05 | 0.05 | 0.05 | 0.05 |
| Refined water | balance | balance | balance | balance | balance |
| Perfume | trace | trace | trace | trace | trace |

*1: Echo Gum, manufactured by Dainippon Pharmaceutical Co., Ltd.
*2: TR-1, manufactured by Goodrich Co., Ltd.

Examples 11 to 15

The respective cosmetic milky lotions (for antiwrinkle, texture-improving, skin roughness, acne and whitening) were prepared according to blend compositions shown in the following Table 10 and Table 11.

All cosmetic milky lotions were highly effective for preventing or treating the targeted symptoms. Further, they were impregnated into publicly known unwoven fabrics to be used in the form of packs and they were highly effective as well.

TABLE 10

Cosmetic milky lotion
(blend unit: % by mass, total amount: 100% by mass)

|  | Example | | | | |
|---|---|---|---|---|---|
|  | 11 Antiwrinkle | 12 Texture improving | 13 Skin roughness | 14 Acne | 15 Whitening |
| N-retinoyl-D-glucosamine (trans isomer) | 2.00 | 1.00 | 1.00 | 2.00 | 2.00 |
| N-retinoyl-D-glucosamine (9-cis isomer) | 0.001 | 0.005 | 0.001 |  | 0.001 |

TABLE 10-continued

Cosmetic milky lotion
(blend unit: % by mass, total amount: 100% by mass)

| | Example | | | | |
|---|---|---|---|---|---|
| | 11 Antiwrinkle | 12 Texture improving | 13 Skin roughness | 14 Acne | 15 Whitening |
| N-retinoyl-D-glucosamine (13-cis isomer) | 0.009 | 0.005 | 0.001 | 0.01 | 0.009 |
| N-oleoyl-D-glucosamine | 1.00 | — | — | 2.00 | — |
| N-linoleoyl-D-glucosamine | — | — | — | — | 0.05 |
| N-lauroyl-D-glucosamine | 1.00 | 1.00 | — | 0.50 | — |
| N-isostearoyl-D-glucosamine | — | — | — | 0.05 | — |
| N-POE (2) hexadecyletheroxy-carbonyl-D-glucosamine | — | — | 1.00 | — | — |
| N-POE (5) octadecyletheroxy-carbonyl-D-glucosamine | — | — | — | — | 0.05 |
| Bentonite | — | — | — | 0.80 | — |
| Montmorillonite | 1.00 | — | — | — | — |
| Hexaglyceryl monostearate | — | — | — | 1.20 | — |
| Decaglyceryl triisostearate | 0.50 | — | — | — | — |
| Diglyceryl monolaurate | — | — | — | 0.50 | — |
| Diglyceryl monostearate | — | 1.50 | 1.50 | — | 1.50 |
| Decaglyceryl monostearate | 1.60 | — | — | — | — |
| Polyoxyethylene sorbitan (20E.O.) monooleate | 3.00 | — | — | — | — |
| Polyoxyethylene-hardened castor oil (100E.O.) | — | 1.00 | 1.00 | — | 1.00 |
| Sorbitan sesquioleate | — | — | — | 3.00 | — |
| Dipotassium glycyrrhizate | — | — | — | 0.20 | — |
| Stearyl glycyrrhetate | 0.20 | 0.20 | 0.20 | — | 0.20 |
| Ellagic acid | — | 0.50 | — | — | — |
| Oxidizing Coenzyme A•8 sodium | 0.30 | — | — | — | — |
| Licorice flavonoid | — | — | — | 0.05 | — |
| Creatinine | 0.20 | 0.20 | — | — | — |
| Isopropyl myristate | — | — | — | 2.00 | — |
| 2-Hexyldecyl isostearate | — | 0.50 | 0.50 | — | 0.50 |
| Ethyl oleate | — | 1.00 | 1.00 | — | 1.00 |
| Methyl polysiloxane *1 | 0.50 | 1.50 | 1.50 | — | 1.50 |
| Decamethylcyclopentasiloxane *2 | — | — | — | 3.00 | — |
| Vegetative squalane | 5.00 | 3.00 | 3.00 | 6.00 | 3.00 |
| Jojoba oil | 3.00 | 1.00 | 1.00 | 1.50 | 1.00 |
| Brierbush oil | — | — | — | 0.50 | — |
| Almond oil | 0.50 | — | — | — | — |
| Macadamia nut oil | 0.50 | — | — | — | — |
| Sunflower oil | 0.50 | — | — | — | — |
| Lecithin | 0.80 | — | — | — | — |
| Behenyl alcohol | 1.00 | 1.50 | 1.50 | — | 1.50 |
| Stearyl alcohol | 1.00 | — | — | 2.00 | — |

*1: SH-200C 10 cs, manufactured by Dow Corning Toray Co., Ltd.
*2: SH245, manufactured by Dow Corning Toray Co., Ltd.

TABLE 11

(continued from Table 10) Cosmetic milky lotion

| | Example | | | | |
|---|---|---|---|---|---|
| | 11 Antiwrinkle | 12 Texture improving | 13 Skin roughness | 14 Acne | 15 Whitening |
| 1,3-Butylene glycol | — | 2.00 | — | — | — |
| 1,2-Pentanediol | — | — | 2.00 | — | 2.00 |
| Dipropylene glycol | 5.00 | 2.00 | 2.00 | 2.00 | 2.00 |
| Polyethylene glycol 300 | — | 3.00 | 3.00 | — | 3.00 |
| Trimethylglycine | 0.50 | 3.00 | 3.00 | — | 3.00 |
| Carboxyvinyl polymer *3 | 0.10 | — | — | 0.12 | — |
| Carboxymethyl cellulose sodium *4 | — | 0.10 | 0.10 | — | 0.10 |
| Xanthan gum *5 | 0.10 | 0.20 | 0.20 | — | 0.20 |
| Propyl paraoxybenzoate | 0.10 | 0.10 | 0.10 | — | 0.10 |
| Methyl paraoxybenzoate | 0.30 | 0.30 | 0.30 | 0.30 | 0.30 |
| Benzalkonium chloride | 0.01 | — | — | — | — |
| Tocopherol acetate | 0.20 | 0.20 | 0.20 | — | 0.20 |
| Silicic anhydride | — | — | — | 0.50 | — |

TABLE 11-continued (continued from Table 10) Cosmetic milky lotion

| | Example | | | | |
|---|---|---|---|---|---|
| | 11 Antiwrinkle | 12 Texture improving | 13 Skin roughness | 14 Acne | 15 Whitening |
| L-arginine | 0.10 | — | — | — | — |
| Darvillea antarctica extract powder | — | 0.20 | 0.20 | — | — |
| 2-Ethylhexyl paramethoxycinnamate | — | — | 0.10 | — | 0.10 |
| 4-tert-butyl-4'-methoxybenzoyl-methane | — | — | 0.25 | — | 0.25 |
| Triisopropanolamine | — | — | — | 0.10 | — |
| Ammonium glycolate | — | 1.00 | — | — | — |
| Ethanol | 2.00 | — | — | 2.00 | — |
| Refined water | balance | balance | balance | balance | balance |
| Perfume | trace | trace | trace | trace | trace |

*3: Hiviswako 105, manufactured by Wako Pure Chemical Industries, Ltd.
*4: CMC1380, manufactured by Daicel Chemical Industries, Ltd.
*5: Monat Gum DA, manufactured by Dainippon Pharmaceutical Co., Ltd.

Examples 16 to 20

The respective cosmetic creams (for antiwrinkle, texture-improving, skin roughness, acne and whitening) were prepared according to blend compositions shown in the following Table 12 and Table 13.

All cosmetic creams were highly effective for preventing or treating the targeted symptoms.

TABLE 12

Cosmetic cream
(blend unit: % by mass, total amount: 100% by mass)

| | Example | | | | |
|---|---|---|---|---|---|
| | 16 Antiwrinkle | 17 Texture improving | 18 Skin roughness | 19 Acne | 20 Whitening |
| N-retinoyl-D-glucosamine (trans isomer) | 2.00 | 1.00 | 1.00 | 2.00 | 2.00 |
| N-retinoyl-D-glucosamine (9-cis isomer) | 0.001 | 0.005 | 0.001 | | 0.001 |
| N-retinoyl-D-glucosamine (13-cis isomer) | 0.009 | 0.005 | 0.001 | 0.01 | 0.009 |
| N-oleoyl-D-glucosamine | | 0.05 | | | 1.00 |
| N-linoleoyl-D-glucosamine | | | | | 0.05 |
| N-lauroyl-D-glucosamine | | 1.00 | | 0.50 | |
| N-isostearoyl-D-glucosamine | | | 1.00 | | |
| N-POE (2) hexadecyletheroxy-carbonyl-D-glucosamine | 0.50 | | 1.00 | | |
| N-POE (5) octadecyletheroxy-carbonyl-D-glucosamine | — | | — | | 0.05 |
| Bentonite | — | — | 1.00 | — | — |
| Saponite | — | — | — | 1.20 | — |
| Hectorite | — | — | 0.80 | — | — |
| Decaglyceryl monostearate | — | 2.00 | — | — | — |
| Tetraglyceryl monoisostearate | 1.00 | — | — | 3.00 | 3.20 |
| Hexaglyceryl monostearate | 0.80 | — | 0.50 | — | — |
| Decaglyceryl distearate | — | — | 0.50 | — | — |
| Decaglyceryl tristearate | — | 0.10 | — | — | — |
| Diglyceryl oleate | — | 0.50 | — | — | — |
| Lipophilic glyceryl monostearate | 1.50 | — | — | — | — |
| Sorbitan monostearate | — | — | 2.50 | 1.00 | 1.00 |
| Polyethylene glycol monostearate (40E.O.) | 1.50 | — | 0.80 | 0.50 | 0.50 |
| Polyoxyethylene-hardened castor oil (100E.O.) | — | 1.00 | — | — | — |
| Polyoxyethylene phytosterol (30E.O.) | — | — | — | 1.00 | 0.50 |

TABLE 12-continued

Cosmetic cream
(blend unit: % by mass, total amount: 100% by mass)

|  | Example | | | | |
|---|---|---|---|---|---|
|  | 16 Antiwrinkle | 17 Texture improving | 18 Skin roughness | 19 Acne | 20 Whitening |
| Stearyl glycyrrhetate | 0.10 | 0.20 | 0.30 | 0.10 | — |
| Dipotassium glycyrrhizate | — | — | — | — | 0.20 |
| Oxidizing Coenzyme A•8 sodium | 0.20 | — | — | 0.50 | — |
| Pantothenyl ethyl ether | 0.50 | — | 0.02 | — | — |
| Creatinine | 0.30 | 0.20 | — | — | — |
| Ellagic acid | — | 0.30 | 0.50 | — | 0.70 |
| Paraffin | — | — | 1.00 | — | 3.00 |
| Cetyl palmitate | 1.00 | 2.00 | 1.20 | — | — |
| Isopropyl palmitate | 1.00 | — | 2.00 | 1.00 | — |
| Isocetyl isostearate | — | 1.00 | — | 2.00 | — |
| 2-Hexyldecyl isostearate | — | — | — | — | 2.00 |
| Decamethylcyclopentasiloxane *1 | — | 1.00 | 5.00 | — | — |
| Methyl polysiloxane *2 | 1.00 | — | 0.50 | 5.00 | — |
| Vegetative squalane | — | 7.00 | — | 10.00 | 5.00 |
| Squalane | 8.00 | — | 3.00 | — | — |

*1: SH245, manufactured by Dow Corning Toray Co., Ltd.
*2: SH-200C 30 cs, manufactured by Dow Corning Toray Co., Ltd.

TABLE 13

(continued from Table 12) Cosmetic cream

|  | Example | | | | |
|---|---|---|---|---|---|
|  | 16 Antiwrinkle | 17 Texture improving | 18 Skin roughness | 19 Acne | 20 Whitening |
| Jojoba oil | 3.00 | 2.00 | — | 2.00 | 3.50 |
| Almond oil | — | 1.00 | — | 1.00 | — |
| Sunflower oil | — | — | — | 1.00 | 1.00 |
| Brierbush oil | 0.05 | — | — | — | — |
| Lecithin | — | 0.50 | — | — | — |
| Cetostearyl alcohol | 3.00 | 5.00 | — | — | — |
| Stearyl alcohol | — | — | 5.00 | 3.00 | — |
| Behenyl alcohol | 0.50 | — | — | — | 3.00 |
| Conc. glycerin | 1.00 | 5.00 | 7.00 | 3.00 | 10.00 |
| 1,3-Butylene glycol | 5.00 | 1.00 | — | 3.00 | — |
| 1,2-Pentanediol | — | — | 2.00 | — | 3.00 |
| Polyethylene glycol 300 | — | — | 3.00 | — | — |
| Dipropylene glycol | 1.00 | 3.00 | 2.50 | — | 5.00 |
| Trimethylglycine | — | — | — | 5.00 | 0.50 |
| L-proline | — | 1.00 | 0.10 | — | — |
| Carboxyvinyl polymer *3 | 0.05 | 0.05 | 0.05 | — | — |
| Transparent soluble xanthan gum *4 | — | 0.10 | — | 0.20 | — |
| Xanthan gum *5 | 0.30 | 0.10 | — | — | 0.20 |
| Propyl paraoxybenzoate | 0.10 | 0.10 | 0.10 | 0.10 | 0.10 |
| Methyl paraoxybenzoate | 0.30 | 0.30 | 0.30 | 0.30 | 0.30 |
| 2-Ethylhexyl paramethoxycinnamate | — | — | 0.10 | — | 0.10 |
| 4-tert-butyl-4'-methoxybenzoyl-methane | — | — | 0.25 | — | 0.25 |
| Natural vitamin E | 0.20 | — | — | 0.20 | — |
| Tocopherol acetate | — | 0.20 | 0.20 | — | 0.20 |
| Citric acid | trace | trace | trace | trace | trace |
| Sodium citrate | trace | trace | trace | trace | trace |
| Disodium ethylenediamine-tetraacetate | 0.10 | 0.10 | 0.10 | 0.10 | 0.10 |
| Triisopropanolamine | 0.10 | 0.10 | 0.10 | 0.10 | 0.10 |
| Darvillea antarctica extract powder | 0.20 | — | — | 0.50 | — |
| Refined water | balance | balance | balance | balance | balance |
| Perfume | trace | trace | trace | trace | trace |

*3: Sintaren M, manufactured by Wako Pure Chemical Industries, Ltd.
*4: Echo Gum T, manufactured by Dainippon Pharmaceutical Co., Ltd.
*5: Monat Gum DA, manufactured by Dainippon Pharmaceutical Co., Ltd.

Examples 21 to 25

The respective ointments (for antiwrinkle, texture-improving, skin roughness, acne and whitening) were prepared according to blend compositions shown in the following Table 14.

All ointments were highly effective for preventing or treating the targeted symptoms.

Evaluation Criteria:

⊚: very good
○: good
Δ: a little good
x: inferior

The results thereof are shown in the following Table 15.

TABLE 14

Ointment
(blend unit: % by mass, total amount: 100% by mass)

| | Example | | | | |
|---|---|---|---|---|---|
| | 21 Antiwrinkle | 22 Acne | 23 Texture improving | 24 Skin roughness | 25 Whitening |
| N-retinoyl-D-glucosamine (trans isomer) | 2.00 | 1.00 | 1.00 | 2.00 | 2.00 |
| N-retinoyl-D-glucosamine (9-cis isomer) | 0.001 | 0.005 | 0.001 | | 0.001 |
| N-retinoyl-D-glucosamine (13-cis isomer) | 0.009 | 0.005 | 0.001 | 0.01 | 0.009 |
| N-oleoyl-D-glucosamine | | 1.00 | 0.05 | | 1.00 |
| N-linoleoyl-D-glucosamine | | | | | 0.05 |
| N-lauroyl-D-glucosamine | | 0.50 | 1.00 | | |
| N-isostearoyl-D-glucosamine | | | | | |
| N-POE (2) hexadecyletheroxy-carbonyl-D-glucosamine | 0.50 | | | 1.00 | |
| N-POE (5) octadecyletheroxy-carbonyl-D-glucosamine | | | | | 0.05 |
| Liquid paraffin | 6.00 | 6.00 | — | — | — |
| Cetanol | 7.00 | 7.00 | — | — | — |
| Polyoxyethylene alcohol ether | 2.00 | 2.00 | — | — | — |
| Stearyl alcohol | — | — | 20.00 | 20.00 | 20.00 |
| Polyoxyethylene (60)-hardened castor oil | — | — | 4.00 | 4.00 | 4.00 |
| Glyceryl monostearate | — | — | 1.00 | 1.00 | 1.00 |
| Propylene glycol | — | — | 12.00 | 12.00 | 12.00 |
| Methyl paraben | 0.02 | 0.02 | 0.05 | 0.05 | 0.05 |
| Butyl paraben | 0.18 | 0.18 | 0.15 | 0.15 | 0.15 |
| Refined water | balance | balance | balance | balance | balance |
| Perfume | trace | trace | trace | trace | trace |

Examples 26 to 28

Creams (for antiwrinkle, acne/whitening and texture-improving/skin roughness) using silicone oils and silicone derivatives base were prepared according to blend compositions shown in the following Table 15. A silicone mixture A shown in the following Table 15 is a paste-like polyether-modified silicone composition obtained by subjecting cross-linking type polyether-modified silicone and methyl polysiloxane to kneading treatment under a shearing force, and a ratio of cross-linking type polyether-modified silicone to methyl polysiloxane in the composition is 1:0.1 to 10:1.

Further, evaluated was use feeling (presence or absence of stickiness and irritative feeling) of the above creams using silicone oils and silicon derivatives base. In the evaluation of the use feeling, the respective creams obtained above were used 0.2 g at a time twice a day on either of left and right cheeks by 10 female subjects of 30 to 35 years old for one month to make sensory evaluation of the presence or absence of sticky feeling and irritative feeling according to four degrees of the following evaluation criteria.

TABLE 15 silicone oil and silicone derivative base-containing cream
(blend unit: % by mass, total amount: 100% by mass)

| | Example | | |
|---|---|---|---|
| | 26 Anti-wrinkle | 27 Acne/whitening | 28 Texture improving/skin roughness |
| N-retinoyl-D-glucosamine (trans isomer) | 2.00 | 2.00 | 2.00 |
| N-retinoyl-D-glucosamine (9-cis isomer) | | 0.001 | 0.0025 |
| N-retinoyl-D-glucosamine (13-cis isomer) | 0.02 | 0.009 | 0.0025 |
| N-POE (5) octadecyletheroxy-carbonyl-D-glucosamine | | 0.50 | |
| N-oleoyl-D-glucosamine | 1.00 | | |
| N-isostearoyl-D-glucosamine | | 0.50 | 1.00 |
| N-lauroyl-D-glucosamine | 0.50 | | 1.00 |

TABLE 15-continued silicone oil and silicone derivative base-containing cream
(blend unit: % by mass, total amount: 100% by mass)

| | Example | | |
|---|---|---|---|
| | 26 Anti-wrinkle | 27 Acne/whitening | 28 Texture improving/skin roughness |
| Silicone mixture A | 8.00 | | |
| Polyether-modified alkyl-modified organosiloxane copolymer | | 1.50 | |
| Polyether-modified organosiloxane | | 1.50 | |
| Polyether-modified silicone | | | 2.50 |
| Caprylic/capric triglyceride | | | 0.50 |
| Lipophilic glyceryl monostearate | | | 0.75 |
| Polyethylene glycol monostearate (75E.O.) | | | 0.25 |
| Hardened castor oil | | | 0.50 |
| Microcrystalline wax | | | 0.50 |
| Silicic anhydride (porous silica) | 5 | 5.00 | |
| Cross-linking type methyl polysiloxane | 0.3 | 0.20 | |
| Decamethylcyclopentasiloxane | 15 | 10.00 | 10.00 |
| Dodecamethylcyclohexasiloxane | 2 | | |
| Methyl polysiloxane | | 5.00 | |
| Squalane | 3 | | 3.00 |
| Isopropyl myristate | | 3.00 | |
| Citrus unshiu peel extract | 0.5 | | |
| Potassium cetylphosphate | | | 0.10 |
| Conc. glycerin | 3 | | 5.00 |
| Dipropylene glycol | | | 5.00 |
| Methyl paraoxybenzoate | | 0.3 | |
| Propyl paraoxybenzoate | | 0.10 | |
| Xanthan gum | | | 0.1 |
| Carboxyvinyl polymer | | | 0.1 |
| Sodium chloride | 0.8 | 0.5 | |
| Ethanol | 6 | | |
| Refined water | balance | balance | balance |
| Perfume | trace | trace | trace |
| Use feeling (absence of stickiness and irrition) | ◎ | ◎ | ◎ |

As apparent from the results shown in Table 15 described above, the respective creams using silicone oils and silicone derivatives base were very good without having stickiness and irritative feeling.

All creams using silicone oils and silicone derivatives base were highly effective for preventing or treating the targeted symptoms.

INDUSTRIAL APPLICABILITY

As described above, the external preparation composition of the present invention can suitably be used for preventing or treating symptoms or diseases related to dermatopathy caused by dryness, UV rays, active oxygen and aging such as wrinkles and sags of the skin, pigmentation of the skin, skin roughness and coarse texture, dyskeratosis such as psoriasis, lichen, ichthyosis, keratosis and Darier's disease and skin diseases such as pustulosis, acne, eczema and atopic dermatitis.

What is claimed is:

1. A method for treating wrinkles and/or acne, and/or for whitening a skin, wherein said method comprises topically applying to the skin of a human being a composition comprising at least one N-retinoyl-D-glucosamine represented by the following Formula (I):

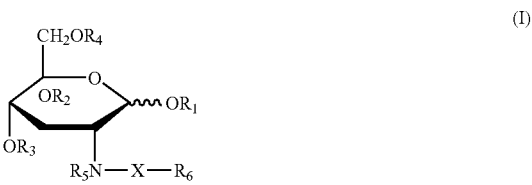

wherein $R_1$, $R_2$, $R_3$, $R_4$ and $R_5$ each represent a hydrogen atom; and $X$-$R_6$ represents a retinoyl group containing a cis stereoisomer in a proportion of 0.5% or more based on the trans stereoisomer.

2. The method of claim 1, wherein said composition further comprises a percutaneous absorption accelerator and/or an additional chemically active substance having a skin care effect.

3. The method of claim 1, wherein said composition further comprises a silicone oil and a silicone derivative.

4. The method of claim 2, wherein said composition further comprises a silicone oil and a silicone derivative.

5. The method of claim 2, wherein said percutaneous absorption accelerator is selected from the group consisting of isopropyl palmitate, isopropyl myristate, diisopropyl adipate, dioctyl succinate, octyldodecyl lactate, oleic acid, ethyl oleate, decyloleate, ottyldodecyloleate, propylene glycol oleate, urea and its derivatives, glycolic acid and its salts, lactic acid and its salts, salicyclic acid, ethanol, isopropanol, propylene glycol, dipropylene glycol, 1,3-butylene glycol, polyethylene glycol, cyclodexitrin, polyethylene glycol/polydimethylsiloxane copolymers, creatine, and combinations thereof.

6. The method of claim 5, wherein said composition further comprises a silicone oil and a silicone derivative.

* * * * *